United States Patent [19]

Korbonits et al.

[11] Patent Number: 4,840,949
[45] Date of Patent: Jun. 20, 1989

[54] OXADIAZOLE-ALKYL-PURINE DERIVATIVES USEFUL AS ANTITUSSIVE AGENTS

[75] Inventors: Dezsö Korbonits, Budapest; Emil Minker, Szeged; Zoltán Vargai, Budapest; Gergely Héja, Budapest; Gábor Kovács, Budapest; Ágnes Gottsegen, Budapest; Sándor Antus, Budapest; Sándor Virág, Budapest; Andrea Bolehovszky, Budapest; Jenö Marton, Budapest; Katalin Mármarosi née Kellner, Biatorbágy; Lóránd Debreczeni, Budapest; László Tardos, Budapest; Péter Körmöczy, Budapest; Vera Gergely, Budapest; Gábor Horváth, Budapest, all of Hungary

[73] Assignee: Chinoin Gyogyszer Es Vegyeszeti Termekek Gyara Rt., Budapest, Hungary

[21] Appl. No.: 107,693

[22] Filed: Oct. 9, 1987

[30] Foreign Application Priority Data

Oct. 9, 1986 [HU] Hungary ............................. 4230/86

[51] Int. Cl.$^4$ ..................... A61K 31/52; C07D 473/06
[52] U.S. Cl. .................. 514/234.2; 514/265; 544/118; 544/270
[58] Field of Search ............... 544/270, 118, 267; 514/234.2, 265

[56] References Cited

U.S. PATENT DOCUMENTS 4,565,817 1/1986 Korbonits et al. .................. 514/263

FOREIGN PATENT DOCUMENTS 0264081 4/1988 European Pat. Off. ........... 544/270

Primary Examiner—Anton H. Sutto
Assistant Examiner—Diana G. Rivers
Attorney, Agent, or Firm—Herbert Dubno; Jonathan Myers

[57] ABSTRACT

The invention relates to new oxidiazole-alkyl-purine-derivatives of the Formula I

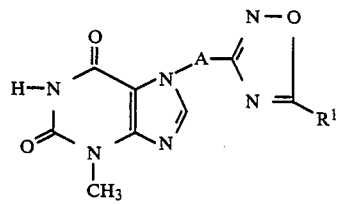

and pharmaceutically acceptable salts thereof wherein A stands for $C_{1-4}$ alkylene and $R^1$ represents $C_{1-6}$ alkyl, hydroxyalkyl, halogenoalkyl, carboxyalkyl, $C_{5-6}$ cycloalkyl or aminoalkyl of the Formula $-(CH_2)_n-NR^2R^3$ in which group n is an integer 1–3; $R^2$ and $R^3$ each stand for hydrogen or $C_{1-4}$ alkyl or together with the adjacent nitrogen atom they are attached to form a 5- or 6-membered nitrogen containing heterocyclic ring which may optionally comprise a further nitrogen atom or an oxygen atom as heteroatom; or $R^1$ stands for phenyl, hydroxyphenyl, carboxyphenyl, benzyl or dimethoxybenzyl The compounds of the Formula I can be prepared by methods known per se and can be used in therapy as antitussive agents.

9 Claims, No Drawings

OXADIAZOLE-ALKYL-PURINE DERIVATIVES USEFUL AS ANTITUSSIVE AGENTS

FIELD OF THE INVENTION

This invention relates to new oxadiazolyl-alkyl-purine derivatives and pharmaceutically acceptable salts thereof, a process for the preparation thereof and pharmaceutical compositions comprising the same.

SUMMARY OF THE INVENTION

The new compounds of the present invention are particularly useful antitussive agents in the treatment of the diseases of the respiratory organs.

The compounds of the present invention are oxadiazolyl-alkyl-derivatives of the Formula I and pharmaceutically acceptable salts thereof

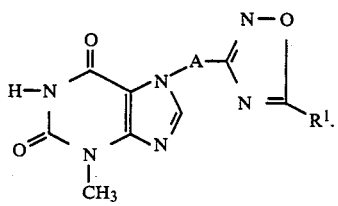

wherein
A stands for $C_{1-4}$ alkylene and
$R^1$ represents $C_{1-6}$ alkyl, hydroxyalkyl, halogenoalkyl, carboxyalkyl, $C_{5-6}$ cycloalkyl or aminoalkyl of the Formula $-(CH_2)_n-NR^2R^3$ in which group n is an integer from 1 to 3; $R^2$ and $R^3$ each stand for hydrogen or $C_{1-4}$ alkyl or together with the adjacent nitrogen atom they are attached to form a 5- or 6-membered nitrogen-containing heterocyclic ring which may optionally comprise a further nitrogen atom or an oxygen atom as heteroatom; or
$R^1$ stands for phenyl, hydroxyphenyl, carboxyphenyl, benzyl or dimethoxybenzyl).

The term "alkyl" encompasses both straight and branched chain groups. The benzyl group is preferably 3,4-dimethoxybenzyl.

The salts of the compounds of the Formula I can be salts formed with inorganic acids (e.g. hydrochloric acid, sulfuric acid, phosphoric acid) or organic acids, e.g. carboxylic or sulfonic acids (e.g. acetic acid, tartaric acid, maleic acid, lactic acid, citric acid, ascorbic acid, benzoic acid, hydroxy benzoyl benzoic acid, nicotinic acid, methanesulfonic acid or toluene sulfonic acid). The said salts are acid addition salts. The compounds of the Formula I also form salts with bases (e.g. alkaline and alkaline earth metals, such as sodium, potassium, calcium, magnesium). The salts may also be complex salts (e.g. salts formed with ethylene diamine).

Organic substances occuring in nature and derivatives thereof have long been used in the treatment of diseases of the organs of respiration as antitussive agents. For this purpose particularly morphine type compounds are used, the most well-known antitussive reresentative thereof being codeine. The said compounds act on the central nervous system in a non-specific manner and have several undesired side-effects. A particularly dangerous side-effect of codeine is the respiration blocking activity. In the last decade efforts have been made to prepare antitussives which in therapeutical doses do not exert this side-effect or possess the side effect only to a very small extent.

As antitussive agents of the above new type certain organic compounds comprising an 1,2,4-oxadiazole ring can be mentioned (e.g. OXOLAMIN and PRENOXDIAZIN).

Recently the group of antitussive agents comprising an 1,2,4-oxadiazole ring has been enriched by a new compound group wherein the 1,2,4-oxadiazole ring is attached to the nitrogen atom in position 7 of the purine structured theophylline through an alkyl chain. In addition to the antitussive effect these compounds exhibit significant respiration improving and broncholytic effect and have a favorable level of toxicity (Hungarian Pat. No. 186,607).

OBJECT OF THE INVENTION

It is the object of the present invention to provide new purine derivatives substituted by an 1,2,4-oxadiazolyl ring which possess stronger therapeutically useful properties than the hitherto known compounds.

DETAILED DESCRIPTION OF THE INVENTION

The above object is achieved by providing new 1,2,4-oxadiazole derivatives of the Formula I as described. It has been found in a surprising manner that the new compounds of the Formula I exhibit an outstandingly strong antitussive effect.

On studying the relationship between chemical structure and therapeutical activity we have come to the unexpected conclusion that in the compounds of the Formula I the purine ring potentiates the antitussive effect of the 1,2,4-oxadiazole moiety to a higher extent than the analoguous derivatives substituted in position 1 by a methyl group.

The compounds of the Formula I differ from the theophylline-oxadiazoles disclosed in Hungarian Pat. No. 186,607 only in the absence of the methyl group on the nitrogen atom in position 1 of the purine ring, the said methyl group being present in the prior art compounds.

The new effect is all the more surprising since the biological activity of theophylline is higher than that of theobromine.

The 1,2,4-oxadiazole ring plays a fundamental role in the outstandingly high antitussive activity as shown by comparative tests carried out with compounds of the Formula II.

Compounds of the Formula II

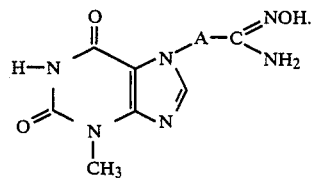

comprise the same purine ring as the compounds of the Formula I but contain no closed 1,2,4-oxadiazole ring. The compounds of the Formula II show practically no antitussive effect.

The antitussive effect of the compounds of the Formula I is so strong that it is higher not only than that of the above mentioned oxadiazole type antitussive agents but also surpasses several times that of codeine.

The further therapeutical advantage of the compounds of the Formula I resides in the favorable level of toxicity.

It is furthermore noteworthy that according to tests carried out on rats and rabbits with the new Formula (I) compounds as opposed to antitussive agents—the compounds of the Formula I exert no respiration blocking effect and moreover have favorable broncho-pulmonal activity.

The aforesaid facts are supported by Table I wherein the $ID_{50}$ mg/kg values of 3,7-dihydro-3-methyl-7-[(5-methyl-1,2,4-oxadiazole-3-yl)-methyl]-1H-purine-2,6-dione (the most simple representative of the compounds of the Formula I); two known 1,2,4-oxadiazole-type antitussive agents, codeine and dextromethorphane (morphine type reference compounds) in the alleviation of coughing caused by a 15% citric acid spray are disclosed. The test compounds are added p.o. one hour before the determination of antitussive activity. As test animal guinea pigs are used. (Method: Arzneimittel Forschung 1966, 617–621). Test compound No. 5 is 2-(3-methyl-xanthine-7-yl)-acetamidoxime (a starting material of the Formula II).

It appears from Table I that the absolute strength of the antitussive effect of compound No. 1 is significantly higher than that of reference compounds Nos. 2–4 and 6. The effect of the xanthinyl amidoxime derivative No. 5 is practically negligible.

TABLE I

Alleviation of coughing caused by 15% citric acid spray on guinea pig, the test compounds are administered orally

| Test Compound No. | Chemical nomenclature of test compound | Antitussive effect, measured 1 hour after oral administration $ID_{50}$ mg/kg |
| --- | --- | --- |
| 1 | 3,7-dihydro-3-methyl-(7-(5-methyl-1,2,4-oxadiazole-3-yl)-methyl)1H—purine-2,6-dione | 8.5 |
| 2 (reference compound) | 3,7-dihydro-1,3-dimethyl-7-[(5-methyl-1,2,4-oxadiazole-3-yl)-methyl]-1H—purine-2,6-dione | 111.2 |
| 3 (reference compound) | 3-(2,2-diphenyl-ethane-1-yl)-5-(-2-piperidino-ethane-1-yl)-1;2,4-oxadiazole.HCl(PRENOXDIAZIN.HCl) | 60.5 |
| 4 (ref. compound) | Codeine.HCl | 65.7 |
| 5 | 2-(3-methyl-xanthine-7-yl)-acetamidoxime | inactive in a dose of 50 mg/kg p.o. |
| 6 (ref. compound) | Dextromethorphan | 29.0 |

The oral antitussive effect of compound No. 1 is very long-lasting, as proved by the data of Table I/A.

TABLE I/A

Antitussive effect of p.o. administered 3,7-dihydro-3-methyl-7-[(5-methyl-1,2,4-oxadiazole-3-yl)-methyl]-1H—purine-2,6-dione on coughing induced by 15% citric acid spray on guinea pig

| Pre-treatment time (H) | $ID_{50}$ mg/kg |
| --- | --- |
| 0.5 | 7.5 |
| 1.0 | 8.5 |
| 2.0 | 14.4 |
| 4.0 | 13.8 |
| 8.0 | 32.6 |

The acute toxicity of compound No. 1 of Table I and that of reference compounds Nos. 2 and 4 disclosed in Table I/B. Test animal: rats; intraperitoneal administration.

TABLE I/B

| Test compound No. (see TABLE I) | Toxicity on rats i.p. $LD_{50}$ mg/kg |
| --- | --- |
| 1 | 700.0 |
| 2 (reference) | 529.7 |
| 4 (reference) | 72.4 |

Compound No. 1 exhibits not only at oral but also at intravenous administration an outstandingly strong antitussive effect. The said compound decreases in dose-dependant manner (administration: 0.5–8.0 MG/KG I.V.) the coughing caused by mechanical stimulation of the trachea bifurcatio on rabbits narcotised by nembutal. After 2 minutes of I.V. administration the $ED_{50}$ value is 2.24 (1.85–2.72) MG/KG calculated according to Lichfield-Wilcoxon. The reference compounds Nos. 4 and 6 possess the same or a somewhat lower antitussive effect. Taking into consideration also the I.O. toxicity data the therapeutical index of the compound No. 1 is ten times more favorable than that of reference compounds Nos. 4 and 6. Other compounds of the Formula I show a similar strong antitussive effect, to that of the compound No. 1 of Table 1.

According to a further aspect of the present invention there is provided a process for the preparation of compounds of the Formula I and pharmaceutically acceptable salts thereof which comprises (a) reacting an amidoxime of the Formula II

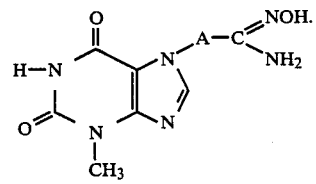

(wherein A is as stated above) with a carboxylic acid of the Formula III $R^4$—CO_2H   (III)

(wherein $R^4$ has the same meaning as $R^1$ or stands for a group which is suitable for the formation of group $R^1$) or a reactive derivative thereof and if desired converting group $R^4$ into group $R^1$; or (b) reacting an amidoxime of the Formula II (wherein A is as stated above) with a carboxylic acid of the Formula III (wherein $R^4$ is as stated above) or a reactive derivative thereof, subjecting the compound of the Formula IV

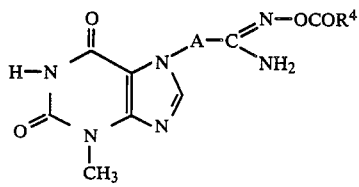

thus obtained (wherein A and $R^4$ are as stated above) to cyclization by dehydration after or without isolation and if desired converting group $R^4$ into group $R^1$; or (c) reacting an oxadiazole derivative of the Formula V

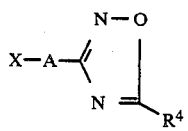

(wherein A and $R^4$ are as stated above and X stands for halogen or a sulfonic acid ester group) in the presence of a basic catalyst with 3-methyl-xanthine of the Formula VI

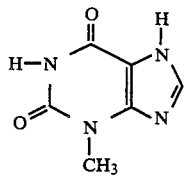

or the sodium or potassium salt thereof and if desired converting group $R^4$ into group $R^1$; or (d) for the preparation of compounds of the Formula I (wherein A stands for $-(CH_2)_2-$ and $R^1$ is as stated above), reacting an olefin of the Formula VII

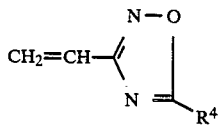

(wherein $R^4$ is as stated above) with 3-methyl-xanthine of the Formula VI in the presence of a basic catalyst, and if desired converting the group $R^4$ into group $R^1$, and if desired converting a compound of the Formula I thus obtained into a a pharmaceutically acceptable salt thereof.

According to process (a) one may proceed preferably by reacting an amidoxime of the Formula II with an ester of the Formula VIII $$R^4CO_2R^5 \qquad (VIII)$$

(wherein $R^4$ is as stated above and $R^5$ stands for alkyl, preferably methyl or ethyl) in the presence of a base (preferably an alkali or alkaline earth metal hydroxide, carbonate or alcoholate, particularly sodium methylate or sodium ethylate) in a polar or apolar organic solvent and/or diluent under heating, preferably at the boiling point of the solvent and/or diluent. As solvent and/or diluent preferably $C_{1-4}$ alcohols, N-alkyl-acid amides (e.g. dimethyl formamide), aromatic hydrocarbons (e.g. benzene, chlorobenzene, preferably toluene or xylene) can be used. If apolar solvents are used, the water and alcohol formed may be advantageously removed by azeotropic distillation.

According to a further preferred form of realization of process (a) an amidoxime of the Formula II is heated with an acid of the Formula III $$R^4-CO_2H \qquad (III)$$

and/or an anhydride thereof in the presence of an organic solvent. As organic solvent preferably aromatic hydrocarbons can be used. One may proceed particularly preferably by using as solvent the acid and/or acid anhydride whereby the said compounds act simultaneously as acylating and cyclizing agent and as reacting medium. Acylation and cyclization can be carried out at 50°–150° C. particularly at 90°–110° C.

The reaction time of process (a) varies between 30 minutes and 24 hours depending on the reactants and solvent used and the reaction temperature.

According to process (b) acylation may be carried out preferably by using an anhydride of the Formula $(R^4CO)_2O$ or an acid halide of the Formula $R^4COX$ (wherein $R^4$ is as stated above and X stands for halogen), preferably an acid chloride, in the presence of an organic solvent and/or diluent (e.g. acetone, pyridine, benzene, dimethyl formamide or when anhydrides are used as acylating agent an excess of the acid anhydride preferably dichloromethane, chloroform etc). If acid halides are used, acylation is advantageously carried out in the presence of an acid binding agent. It is preferred to use inorganic acid binding agents (e.g. alkali metal or alkaline earth metal carbonates, such as sodium carbonate, potassium carbonate or calcium carbonate, or hydrogen carbonates eg. sodium hydrogen carbonate etc) but organic acid binding agents (e.g. tertiary amines, such as pyridine or triethyl amine) may be used as well. If acylating agents are used in which $R^4$ is a basic group, the compound of the Formula IV

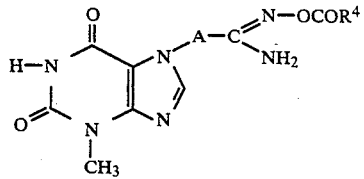

may also serve as acid binding agent.

According to process (b) the oxadiazole ring is formed in a polar organic solvent and/or water as solvent and/or diluent or in an apolar solvent and/or diluent or in the absence of a solvent by pyrolysis.

Cyclization of the compound of the Formula IV is preferably accomplished at a pH value of 6–8. The said pH is advantageously adjusted by inorganic or organic bases (preferably sodium carbonate or triethyl amine). It is particularly preferred to use a Britton-Robinsom buffer. Cyclization of water soluble compounds of the Formula IV can be preferably carried out in water at pH 7.

According to method (c) a compound of the Formula V

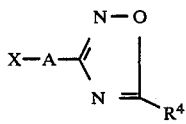

(wherein A is as stated above and X stands for halogen or a sulfonic acid ester group) is reacted with 3-methyl-xanthine of the Formula VI

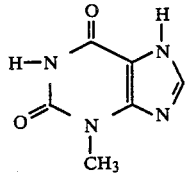

in an organic solvent and/or diluent (preferably dimethyl formamide or an alcohol, preferably n-butanol) in the presence of an inorganic base (e.g. an alkali hydroxide sodium hydroxide preferably, or potassium hydroxide; or an alkali carbonate e.g. sodium or potassium carbonate) or an organic base (e.g. pyridine, triethyl amine or piperidine). One may also proceed by reacting the compound of the Formula V with the sodium or potassium salt of the 3-methyl-xanthine of the Formula VI. The above reactions may be carried out in solution, or suspension, preferably under heating. In the compounds of the Formula Ia

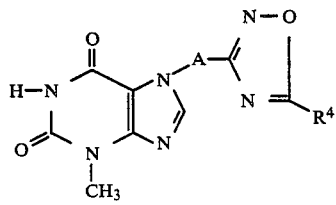

thus obtained the $R^4$ group may be converted, if desired, into an $R^1$ group.

According to method (d) compounds of the Formula IB

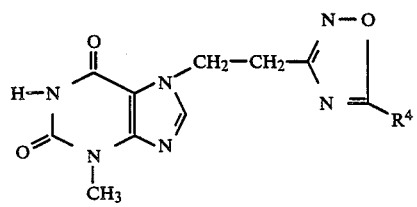

(i.e. compounds of the Formula I (wherein A is —(CH$_2$)$_2$—) are prepared by reacting a compound of the Formula VII

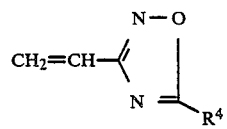

(wherein $R^4$ is as stated above) with 3-methyl-xanthine in the presence of a basic catalyst, preferably a quaternary ammonium hydroxide, particularly Triton-B in an organic solvent and/or diluent under heating. In the compound of the Formula Ia thus obtained the $R^4$ group may be transformed, if desired, into the $R^1$ group.

The 3-methyl-xanthine-7-yl-alkane carboxylic acid amidoximes of the Formula II used as starting material in processes (a) and (b) can be prepared by known methods by reacting the corresponding 3-methyl-xanthine-7-yl-carbonitrile with hydroxylamine under heating in methanol or ethanol or aqueous methanol or ethanol.

The oxadiazoles of the Formula V used as starting material in process (c) can be prepared by methods known per se by reacting the corresponding 3-(w-hydroxyalkyl)-1,2,4-oxadiazole with thionyl chloride, tosyl chloride or mesyl chloride (J. Chem. Res. (M) 1979, 801).

The starting olefins of the Formula VII used in process (d) can also be prepared by known methods (J. Chem. Res. (M) 1979, 801).

Compounds of the Formula Ia and IV, wherein $R^1$ or $R^4$ stands for halogenoalkyl, can be prepared from the amidoximes of the Formula II by reacting same with the corresponding halogenoalkane carboxylic acid chlorides in a manner known per se (Hungarian Pat. No. 186,607).

Compounds of the Formula I, wherein $R^1$ stands for aminoalkyl, can be prepared not only by process (a) but also by subjecting the corresponding compound of the Formula Ia and IV, wherein $R^4$ is halogenoalkyl, to a substitution reaction, or substitution reaction and cyclization respectively, with the corresponding amine in a manner known per se (Hungarian Pat. No. 186,607).

According to a further aspect of the present invention there are provided pharmaceutical compositions comprising as active ingrdient at least one compound of the Formula I or a pharmaceutically acceptable salt thereof in admixture with suitable inert carriers. The active ingredient can be put up in conventional forms e.g. syrups, tablets, pills, coated pills, dragées, capsules, suppositories, injections etc. The pharmaceutical compositions contain known and generally used solvents, diluents, carriers, excipients etc. The said pharmaceutical compositions are prepared by known methods of pharmaceutical industry.

The active ingredient content of the pharmaceutical compositions according to the present invention amounts to 0.1–100%, preferably 1–30%. The daily dose may be generally 2–2000 mg, depending on the mode of application, the age and body weight of the patient, etc.

SPECIFIC EXAMPLES

Further details of the present invention are to be found in the following Examples without limiting the scope of protection to the said Examples.

EXAMPLE 1

35.0 g (0.25 mole) of 3-methyl-xanthine (Chem. Ber. 83, 209 1950) are dissolved in 81.4 ml (0.25 mole) of a 10% sodium hydroxide solution under shaking; crystallization takes place within some minutes. Water is distilled off in vacuo and the traces of water are removed by azeotropic distillation with toluene. The residue is suspended in 35 ml of dimethyl formamide, whereupon a solution of 18.9 g (0.25 mole) of chloroacetonitrile in 80 ml of dimethyl formamide is added dropwise at 100°

C. within 30 minutes. The reaction mixture is stirred at 100° C. for a further hour, filtered until hot, the precipitate (sodium chloride) is washed with hot dimethyl formamide and the united solutions are evaporated to dryness under reduced pressure. The residue is treated with 100 ml of acetone, the crystals are filtered by suction and throughly washed with acetone. The 7-cyanomethyl-3-methyl-xanthine (m.p.: 285°–287° C.) thus obtained can be used in further reactions.

EXAMPLE 2

To a solution of 3.2 g of hydroxylamine-hydrochloride and 36 ml of water 2.5 g of sodium hydrogen carbonate are added in portions. To the solution thus obtained 10.0 g of 7-cyanomethyl-3-methyl-xanthine and 30 ml of ethanol are added, the mixture is stirred at 80° C. for 3 hours. After cooling the precipitated 2-(3-methyl-xanthine-7-yl)-acetamidoxime is filtered by suction and washed with some cold water. Yield 11.0 g, 86%, m.p.: above 320° C.

$^1$H-NMR(DMSO-$d_6$): 3.55(s, 3H, 3-Me); 4.85(s, 2H, NCH$_2$—), 8.03(s, 1H, 8-H); 9.79(s, 1H, N-OH); 11.21(bs, 1H, 1-NH).

EXAMPLE 3

A mixture of a sodium ethylate solution prepared from 6.76 g of metallic sodium and 290 ml of anhydrous ethanol, 35 g of 2-(3-methyl-xanthine-7-yl)-acetamidoxime and 43.0 g of ethyl acetate is heated to boiling under stirring for 4 hours. The hot reaction mixture is filtered, the filtrate is evaporated in vacuo and the residue is dissolved in 200 ml of water. The pH of the solution is adjusted to 7 by adding 10% hydrochloric acid, the precipitate is filtered by suction and crystallized twice from water. Thus, 18.0 g of 3,7-dihydro-3-methyl-7-([5-methyl-1,2,4-oxadiazole-3-yl]-methyl)-1H-purine-2,6-dione are obtained, m.p.: 262°–264° C.

$^1$H-NMR(DMSO-$d_6$): 2.57(s, 3H, 5-Me); 3.37(s, 3H, 3-Me); 5.66(s, 2H, —CH$_2$); 8.18(s, 1H, 6-H); 11.19(bs, 1H, 1-NH).

EXAMPLE 4

A mixture of 3.76 g of (20 millimoles) of 3-methylxanthine-sodium, 100 ml of dimethyl formamide and 2.60 g (19.6 millimoles) of 3-chloromethyl-5-methyl-1,2,4-oxadiazole is stirred at 100° C. for one hour and a half. The hot reaction mixture is filtered and to the filtrate 50 ml of methanol are added. Thus 3.65 g of 3,7-dihydro-3-methyl-7-([5-methyl-1,2,4-oxadiazole-3-yl]-methyl)-1H-purine-2,6-dione are obtained, m.p.: 262°–264° C. Yield: 69%.

EXAMPLE 5

A solution of 3.7 g of 2-(3-methyl-xanthine 7-yl)acetamidoxime and 45.0 ml of acetic anhydride is stirred at 140° C. for an hour. The cooled solution is diluted with water to tenfold volume, and stirred for 30 minutes. The precipitated O-acetyl-2-(3-methyl-xanthine-7-yl)-acetamidoxime is filtered by suction, and washed with some methanol. Yield 3.6 g, m.p.: above 220° C.

$^1$H-NMR (DDMSO-$d_6$): 2.01(s, 3H, OAc), 3.34(s, 3H, 3Me), 4.97(s, 2H, NCH$_2$—), 6.70(bs, 2H, NH$_2$), 8.07 (s, 1H, 6-H), 11.24 (bs, 1H, 1-NH).

EXAMPLE 6

2.0 g of O-acetyl-2-(3-methyl-xanthine-7-yl)-acetamidoxime are stirred in a mixture of 160 ml of a Britton-Robinson buffer (pH 7) and 200 ml of dimethyl formamide at 95° C. for 6 hours. The reaction mixture is evaporated in vacuo and the residue is crystallized from water. Thus 1.22 g of 3,7-dihydro-3-methyl-7-([5-methyl-1,2,4-oxadiazole-3-yl]-methyl)-1H-purine-2,6-dione are obtained. M.p.: 262°–264° C.

EXAMPLE 7

A solution of 2.38 g of 2-(3-methyl-xanthine-7-yl)acetamidoxime in 40.0 ml of anhydrous acetone is acylated with a solution of 1.13 g of chloroacetyl chloride aand 5.0 ml of acetone in the presence of 0.86 g of sodium hydrogen carbonate. Thus 2.1 g of O-chloroacetyl-2-(3-methyl-xanthine-7-yl)acetamidoxime are obtained. The product is heated at 105° C. and 133 Pa until constant weight for 40 minutes. The residue is crystallized from methanol. Thus 1.6 g of 3,7-dihydro-3-methyl-7-([5-chloromethyl-1,2,4-oxadiazole-3-yl]-methyl)-1H-purine-2,6-dione are obtained.

EXAMPLE 8

(a) A mixture of 1.5 g of 3-([3-methyl-xanthine-7-yl]-methyl)-5-chloromethyl-1,2,4-oxadiazole, 10 ml of diethyl amine and 10 ml of toluene is heated on a water bath under stirring for 8 hours in a closed flask equipped with magnetic stirrer. The mixture is evaporated, washed with water, dissolved in 5 ml of hot ethanol, and clarified with activated charcoal. The hydrochloride salt is formed by adding ethanol containing hydrogen chloride. After crystallization from water 1.4 g of 3,7-dihydro-3-methyl-7-([5-diethylaminomethyl-1,2,4-oxadiazole-3-yl]-methyl)-1-purine-2,6-dione-hydrochloride are obtained.

(b) 1.41 g of O-chloroacetyl-2-(3-methyl-xanthine-7-yl)acetamidoxime prepared according to Example 7 are dissolved in 15 ml of toluene, whereupon 1.5 ml of diethyl amine are added dropwise under vigorous stirring. The reaction mixture is heated to boiling for 8 hours, and evaporated. The residue is washed with water and the hydrochloride salt is formed in ethanol. After crystallization from water 1.2 g of 3,7-dihydro-3-methyl-7-([5-diethylaminomethyl-1,2,4-oxadiazole-3-yl]-methyl)-1H-purine-2,6-dione-hydrochloride are obtained.

(c) A mixture of 2.38 g of 2-(3-methyl-xanthine-7-yl)acetamidoxime 3.0 g of diethylamino acetyl chloride and 20 ml of pyridine is stirred at a temperature not exceeding 20° C., whereupon the reaction mixture is heated on a water bath for 2 hours. The reaction mixture is evaporated, the residue is washed with water and the hydrochloride salt is formed in ethanol. After crystallization from water 2.1 g of 3-([3-methyl-xanthine-7-yl]methyl)-5-diethylaminomethyl-1,2,4-oxadiazole-hydrochloride are obtained.

(d) A mixture of 2.38 g of 2-(3-methyl-xanthine-7-yl)acetamidoxime, 200 ml of toluene, 1.36 g of sodium ethylate and 3.46 g of ethyl-β-diethyl-amino-propionate is heated to boiling under stirring in a flask equipped with a water separator for 12 hours. The reaction mixture is evaporated in vacuo, the pH is adjusted to 7, the precipitate is washed with water, dried and the hydrochloride salt is formed in ethanol. Thus 2.0 g of 3,7-dihydro-3-methyl-7-[(5-diethylaminomethyl-1,2,4-oxadiazole-3-yl)-methyl]-1H-purine-2,6-dione-hydrochloride are obtained.

EXAMPLE 9

A solution of 2.38 g of 2-(3-methyl-xanthine-7-yl)acetamidoxime in 25 ml of ethanol is admixed with a solution of 0.46 g of metallic sodium in 25 ml of ethanol and 3.02 g of ethyl cyclohexane carboxylate. The reaction mixture is heated to boiling under stirring for 10 hours, then evaporated. The residue is admixed with water and the pH is adjusted to 7. The precipitate is crystallized from aqueous ethanol. Thus 2.51 g of 3,7-dihydro-3-methyl-7-([5-cyclohexyl-1,2,4-oxadiazole-3-yl]methyl)-1H-purine-2,6-dione are obtained, m.p.: 245°–248° C.

EXAMPLE 10

238 g of 2-(3-methyl-xanthine-7-yl)-acetamidoxime are reacted with 3.28 g of ethyl phenyl acetate and sodium ethylate in ethanol in an analogous manner to the preceeding Example. Thus 2.7 g of 3,7-dihydro-3-methyl-7-([5-benzyl-1,2,4-oxadiazole-3-yl]-methyl)-1H-purine-2,6-dione are obtained, m.p.: 188°–190° C.

EXAMPLE 11

A mixture of 2.52 g of 3-(3-methyl-xanthine-7-yl)propionic acid amide oxime, 4.0 ml of ethyl acetate and a solution of 0.46 g of metallic sodium in 25 ml of ethanol is heated to boiling under stirring for 5 hours. The hot reaction mixture is filtered and the filtrate is evaporated. The residue is treated with 20 ml of water, the pH is adjusted to 7 and the precipitated product is crystallized from water. Thus 1.7 g of 3.7-dihydro-3-methyl-7-(2-[5-methyl-1,2,4-oxadiazole-3-yl]-ethane-1-yl)-1H-purine-2,6-dione are obtained, m.p.: 258°–260° C.

EXAMPLE 12

A mixture of 2.52 g of 3-(3-methyl-xanthine-7-yl)propionic acid amidoxime, 25 ml of toluene, 1.12 g of powdered potassium hydroxide and 3.70 g of ethyl-β-piperidino-propionate is heated to boiling under stirring under a water separator for 10 hours. The reaction mixture is evaporated, the residue is treated with water, the pH is adjusted to 7, the precipitated product is washed with water and converted into the hydrochloride salt in ethanol. Thus 2.6 g of 3,7-dihydro-3-methyl-7-{2-(5-[2-piperidino-ethane-1-yl]-1,2,4-oxadiazole-3-yl)-ethane-1-yl}-1H-purine-2,6-dione-hydrochloride are obtained.

EXAMPLE 13

A mixture of 2.66 g of 4-(3-methyl-xanthine-7-yl)-butyric acid amidoxime, 4.0 ml of ethyl acetate and a solution of 0.46 g of metallic sodium in 25 ml of ethanol is heated to boiling for 6 hours. The reaction mixture is worked up as described in Example 3. Thus 1.8 g of 3,7-dihydro-3-methyl-7-(3-[5-methyl-1,2,4-oxadiazole-3-yl]-propane-1-yl)-1H-purine-2,6-dione are obtained.

EXAMPLES 14–34

The compounds enumerated in Table II are prepared in an analogous manner to Examples 1-13. In the said Table II the No. of the Example, the definition of symbols A and $R^1$ and reference to the method are disclosed.

TABLE II

| No. of Example | A | $R^1$ | Method (No. of Example) |
|---|---|---|---|
| 14 | —CH$_2$— | CH$_3$CH$_2$— | 3 |
| 15 | —CH$_2$— | CH$_3$CH$_2$CH$_2$— | 3 |
| 16 | —CH$_2$— | CH$_3$(CH$_2$)$_3$— | 3 |
| 17 | —CH$_2$— | CH$_3$(CH$_2$)$_4$— | 4 |
| 18 | —CH$_2$— | (CH$_3$)$_2$CH— | 3 |
| 19 | —CH$_2$— | HOCH$_2$CH$_2$— | 3 |
| 20 | —CH$_2$ | —CH$_2$N(piperidinyl) | 8 |
| 21 | —CH$_2$ | —CH$_2$—N(morpholinyl) | 8 |
| 22 | —CH$_2$— | —CH$_2$—(2,3-dimethoxyphenyl) | 3 |
| 23 | —CH$_2$ | —(CH$_2$)$_3$COOH | 3 |
| 24 | —CH$_2$— | phenyl | 3 |
| 25 | —CH$_2$— | 2-hydroxyphenyl | 3 |
| 26 | —CH$_2$— | 2-carboxyphenyl | 6 |
| 27 | —CH$_2$—CH$_2$— | (C$_2$H$_5$)$_2$NCH$_2$— | 8 |
| 28 | —CH$_2$—CH$_2$— | piperidinyl-N—(CH$_2$)$_2$— | 8 |
| 29 | —CH$_2$—CH$_2$— | (C$_2$H$_5$)$_2$N(CH$_2$)$_2$— | 8 |
| 30 | —(CH$_2$)$_3$— | (C$_2$H$_5$)$_2$N(CH$_2$)$_2$— | 8 |
| 31 | —(CH$_2$)$_3$— | piperidinyl-N—(CH$_2$)$_2$— | 8 |
| 32 | —(CH$_2$)$_4$— | CH$_3$— | 4 |
| 33 | —(CH$_2$)$_4$— | (C$_2$H$_5$)$_2$N(CH$_2$)$_2$— | 8 |
| 34 | —(CH$_2$)$_4$— | piperidinyl-N—(CH$_2$)$_2$— | 8 |

EXAMPLE 35

(a) Tablets

| Component | Amount, g |
| --- | --- |
| 3-[(3-methyl-xanthine-7-yl)-methyl]-5-methyl-1,2,4-oxadiazole | 10.0 |
| Wheat starch | 130.0 |
| Calcium phosphate | 199.0 |
| Magnesium stearate | 1.0 |
| Total weight | 340.0 |

The above components are admixed, the powdered mixture is pressed to 100 tablets, weighing 340 mg each, in a manner known per se. Each tablet contains 10 mg of the active ingredient.

(b) Dragees

| Component | Amount, g |
| --- | --- |
| 3-[(3-methyl-xanthine-7-yl)-methyl]-5-methyl-1,2,4-oxadiazole | 50.0 |
| Carboxymethyl cellulose | 300.0 |
| Stearic acid | 20.0 |
| Cellulose acetate phthalate | 30.0 |
| Total weight | 400.0 |

A mixture of the active ingredient, carboxymethyl cellulose and stearic acid is thoroughly admixed with a solution of the celulose acetate phthalate in 200 ml of ethyl acetate. From this mixture dragées weighing 400 mg are pressed and the core is coated with 5% aqueous polyvinyl pyrrolidone in a known manner. Each dragée contains 50 ml of the active ingredient.

(c) Syrup

| Component | Amount, g |
| --- | --- |
| 3-(3-[3-methyl-xanthine-7-yl]-propane-1-yl)-5-(2-diethylamino-ethane-1-yl)-1,2,4-oxadiazole-hydrochloride | 5 g |
| Lemon Syrup | 200 ml |
| Benzoic acid solution | 20 ml |
| Water | 100 ml |
| Sugar syrup ad | 1000 ml |

The active ingredient is dissolved in water with warming, whereupon 500 ml of sugar syrup and the other components are added and the mixture is filled up to 1000 ml with sugar syrup. The active ingredient content of the syrup amounts to 5 mg/ml.

We claim:
1. A compound of the Formula I

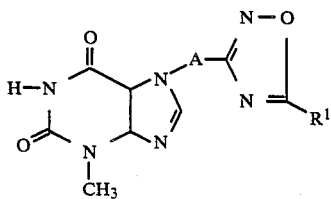

wherein
A stands for $C_{1-4}$ alkylene and
$R^1$ represents $C_{1-6}$ alkyl, hydroxyalkyl, halogenoalkyl, carboxyalkyl, $C_{5-6}$ cycloalkyl or aminoalkyl of the general Formula $-(CH_2)_n-NR^2R^3$ in which group n is an integer from 1-3;
$R^2$ and $R^3$ each stand for hydrogen or $C_{1-4}$ alkyl or together with the adjacent nitrogen atom they are attached to form a 5- or 6-membered nitrogen containing heterocyclic ring which can optionally contain an oxygen atom or a second nitrogen atom; or
$R^1$ stands for phenyl, hydroxyphenyl, carboxyphenyl, benzyl or dimethoxybenzyl;
or a physiologically acceptable acid addition salts or salt formed with inorganic bases thereof.

2. A compound or pharmaceutically acceptable salt thereof as defined in claim 1 selected from the group which consists of:
3,7-dihydro-3-methyl-7-({5-methyl-1,2,4-oxadiazole-3-yl}-methyl)-1H-purine-2,6-dione;
3,7-dihydro-3-methyl-7-({5-(ethane-1-yl)-1,2,4-oxadiazole-3-yl}-methyl)-1H-purine-2,6-dione;
3,7-dihydro-3-methyl-7-({5-(propane-1-yl)-1,2,4-oxadiazole-3-yl}-methyl)-1H-purine-2,6-dione;
3,7-dihydro-3-methyl-7-({5-(butane-1-yl)-1,2,4-oxadiazole-3-yl}-methyl)-1H-purine-2,6-dione;
3,7-dihydro-3-methyl-7-({5-(pentane-1-yl)-1,2,4-oxadiazole-3-yl}-methyl)-1H-purine-2,6-dione;
3,7-dihydro-3-methyl-7-({5-(propane-2-yl)-1,2,4-oxadiazole-3-yl}-methyl)-1H-purine-2,6-dione;
3,7-dihydro-3-methyl-7-({5-cyclohexyl-1,2,4-oxadiazole-3-yl}-methyl)-1H-purine-2,6-dione;
3,7-dihydro-3-methyl-7-({5-chloromethyl-1,2,4-oxadiazole-3-yl}-methyl)-1H-purine-2,6-dione;
3,7-dihydro-3-methyl-7-({5-(2-hydroxy-ethane-yl)-1,2,4-oxadiazole-3-yl}-methyl)-1H-purine-2,6-dione;
3,7-dihydro-3-methyl-7-({5-diethylaminomethyl-1,2,4-oxadiazole-3-yl}-methyl)-1H-purine-2,6-dione;
3,7-dihydro-3-methyl-7-({5-piperidinomethyl-1,2,4-oxadiazole-3-yl}-methyl)-1H-purine-2,6-dione;
3,7-dihydro-3-methyl-7-({5-morpholinomethyl-1,2,4-oxadiazole-3-yl}-methyl)-1H-purine-2,6-dione;
3,7-dihydro-3-methyl-7-({5-benzyl-1,2,4-oxadiazole-3-yl}-methyl)-1H-purine-2,6-dione;
3,7-dihydro-3-methyl-7-({5-(3,4-dimethoxybenzyl)-1,2,4-oxadiazole-3-yl}-methyl)-1H-purine-2,6-dione;
3,7-dihydro-3-methyl-7-({5-(3-carboxy-propane-1-yl)-1,2,4-oxadiazole-3-yl}-methyl)-1H-purine-2,6-dione;
3,7-dihydro-3-methyl-7-({5-phenyl-1,2,4-oxadiazole-3-yl}-methyl)-1H-purine-2,6-dione;
3,7-dihydro-3-methyl-7-({5-(2-hydroxyphenyl)-1,2,4-oxadiazole-3-yl}-methyl)-1H-purine-2,6-dione;
3,7-dihydro-3-methyl-7-({5-(2-carboxypenyl)-1,2,4-oxadiazole-3-yl}-methyl)-1H-purine-2,6-dione;
3,7-dihydro-3-methyl-7-(2-{5-methyl-1,2,4-oxadiazole-3-yl}-ethane-1-yl)-1H-purine-2,6-dione;
3,7-dihydro-3-methyl-7-(2-({5-diethylaminomethyl-1,2,4-oxadiazole-3-yl}-ethane-1-yl)-1H-purine-2,6-dione;
3,7-dihydro-3-methyl-7-(2-[5-piperidinomethyl-1,2,4-oxadiazole-3-yl}-ethane-1-yl)-1H-purine-2,6-dione;
3,7-dihydro-3-methyl-7-(2-{5-(2-piperidino-ethane-1-yl)-1,2,4-oxadiazole-3-yl}-ethane-1-yl)-1H-purine-2,6-dione;
3,7-dihydro-3-methyl-7-(2-({5-(2-diethylamino-ethane-1-yl)-1,2,4-oxadiazole-3-yl}-ethane-1-yl)-1H-purine-2,6-dione;
3,7-dihydro-3-methyl-7-(3-{5-methyl-1,2,4-oxadiazole-3-yl}-propane-1-yl)-1H-purine-2,6-dione;

3,7-dihydro-3-methyl-7-(3-{5-(2-diethylamino-ethane-1-yl}-1,2,4-oxadiazole-3-yl}-propane-1-yl)-1H-purine-2,6-dione;

3,7-dihydro-3-methyl-7-(3-{5-(2-piperidino-ethane-1-yl}-1,2,4-oxadiazole-3-yl}-propane-1-yl)-1H-purine-2,6-dione;

3,7-dihydro-3-methyl-7-(4-{5-methyl-1,2,4-oxadiazole-3-yl}-butane-1-yl)-1H-purine-2,6-dione;

3,7-dihydro-3-methyl-7-(4-{5-(2-diethylamino-ethane-yl)-1,2,4-oxadiazole-3-yl}-butane-1-yl)-1H-purine-2,6-dione;

3,7-dihydro-3-methyl-7-(4-{5-(2-piperidino-ethane-1-yl}-1,2,4-oxadiazole-3-yl}-butane-1-yl}-1H-purine-2,6-dione.

3. A compound of the Formula (I)

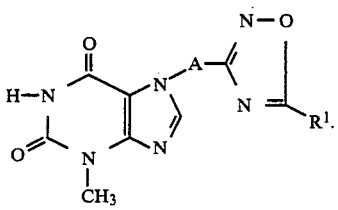

wherein

A is $C_1$ to $C_4$ alkylene;

$R^1$ is $C_1$ to $C_6$ alkyl, hydroxyalkyl, halogenalkyl, carboxyalkyl, $C_5$ to $C_6$ cycloalkyl, or aminoalkyl of the Formula —$(CH_2)_n$—$NR^2R^3$ in which group n is an integer from 1 to 3; and $R^2$ and $R^3$ are each hydrogen or $C_1$ to $C_4$ alkyl or together with the adjacent nitrogen atom they are attached to form a 5- or 6-membered nitrogen-containing heterocyclic ring which can optionally contain an oxygen atom or a second nitrogen atom;

or a physiologically acceptable acid addition salt or salt formed with an inorganic base.

4. A compound of the Formula (I)

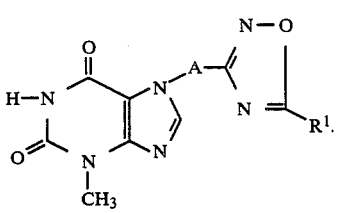

wherein

A is $C_1$ to $C_4$ alkylene;

$R^1$ is $C_1$ to $C_6$ alkyl, or aminoalkyl of the Formula —$(CH_2)_n$—$NR^2R^3$ in which group n is an integer from 1 to 3; and $R^2$ and $R^3$ are each hydrogen or $C_1$ to $C_4$ alkyl or together with the adjacent nitrogen atom they are attached to form a 5- or 6-membered nitrogen-containing heterocyclic ring which can optionally contain an oxygen atom or a second nitrogen atom;

or a physiologically acceptable acid addition salt or salt formed with an inorganic base.

5. A compound of the Formula (I)

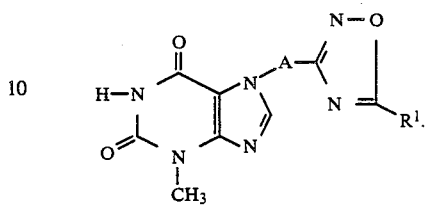

wherein

A is $C_1$ to $C_4$ alkylene;

$R^1$ is $C_1$ to $C_6$ alkyl, or aminoalkyl of the Formula —$(CH_2)_n$—$NR^2R^3$ in which group n is an integer from 1 to 3; and $R^2$ and $R^3$ are each hydrogen or $C_1$ to $C_4$ alkyl or together with the adjacent nitrogen atom they are attached to form a piperidino or morpholino group;

or a physiologically acceptable acid addition salt or salt formed with an inorganic base.

6. A compound of the Formula (I)

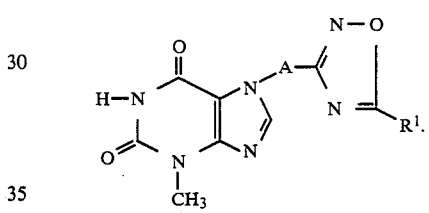

wherein

A is $C_1$ to $C_4$ alkylene;

$R^1$ is $C_1$ to $C_6$ alkyl or aminoalkyl of the Formula —$(CH_2)_n$—$NR^2R^3$ in which group n is an integer from 1 to 3; and $R^2$ and $R^3$ are each hydrogen or $C_1$ to $C_4$ alkyl;

or a physiologically acceptable acid addition salt or salt formed with an inorganic base.

7. 3,7-dihydro-3-methyl-7-[(5-methyl-1,2,4-oxadiazole-3-yl)-methyl]-1H-purine-2,6-dione or a pharmaceutically acceptable salt thereof formed with an inorganic base.

8. An antitussive composition comprising as active ingredient an antitussively effective amount of a compound of the Formula I as defined in claim 1 or a pharmaceutically acceptable salt thereof in admixture with a suitable inert carrier.

9. An antitussive method of treatment which comprises the step of administering to a susceptible animal subject an antitussively effective amount of a compound as defined in claim 1.

* * * * *

UNITED STATES PATENT AND TRADEMARK OFFICE
CERTIFICATE OF CORRECTION

PATENT NO. : 4,840,949

DATED : 20 June 1989

INVENTOR(S) : Dezso KORBONITS et al

It is certified that error appears in the above-identified patent and that said Letters Patent is hereby corrected as shown below:

Item [75] Third Inventor's name to read:

-- Zoltan VARGA I --.

Signed and Sealed this

Sixteenth Day of October, 1990

*Attest:*

HARRY F. MANBECK, JR.

*Attesting Officer*     *Commissioner of Patents and Trademarks*